(12) United States Patent
Lee et al.

(10) Patent No.: US 6,326,644 B1
(45) Date of Patent: Dec. 4, 2001

(54) CONTACT LIGHT EMITTING DEVICE

(75) Inventors: Ju Hyun Lee; Vladimir Vlaskin; Young Kee Ryu, all of Choongchungnam-do (KR)

(73) Assignee: Mirae Corporation, Chunan-shi (KR)

( * ) Notice: Subject to any disclaimer, the term of this patent is extended or adjusted under 35 U.S.C. 154(b) by 0 days.

(21) Appl. No.: 09/311,276

(22) Filed: May 14, 1999

(30) Foreign Application Priority Data

| | | | |
|---|---|---|---|
| May 15, 1998 | (KR) | ............................ | 98-17652 |
| Jun. 23, 1998 | (KR) | ............................ | 98-23748 |
| Sep. 7, 1998 | (KR) | ............................ | 98-36742 |
| Dec. 23, 1998 | (KR) | ............................ | 98-57701 |

(51) Int. Cl.[7] .................. H01L 33/00; H01J 1/62
(52) U.S. Cl. .................. 257/91; 257/98; 257/99; 257/103; 313/506
(58) Field of Search ................ 257/99, 98, 103, 257/91, 92; 313/503, 504, 506, 509

(56) References Cited

U.S. PATENT DOCUMENTS 5,105,238 * 4/1992 Nikaido et al. ................ 257/99

FOREIGN PATENT DOCUMENTS 1997-019282 12/1998 (KR) .

* cited by examiner

*Primary Examiner*—Minh Loan Tran
(74) *Attorney, Agent, or Firm*—Fleshner & Kim, LLP

(57) ABSTRACT

A contact light emitting device embodying the invention includes a transparent electrode layer and a luminescence layer. The electrode layer and the luminescence layer are configured such that an electric field can be generated between the electrode layer and an object to be imaged. When the object to be imaged is brought adjacent the luminescence layer, the luminescence layer emits light, which is then converted into an electrical signal.

37 Claims, 4 Drawing Sheets

| Sample | Mixing Ratio (wt.%) |
|---|---|
| Polymer paste | 25~35 |
| Retarder | 25~29 |
| Luminance Powder | 36~50 |

[Fig. 4]

| Sample | Mixing Ratio (wt.%) |
|---|---|
| Polyurethane or Poly vinyl butyral | 30 |
| Ethyllene glycon monoethyl ether acetate | 70 |

[Fig. 5]

| Sample | Mixing Ratio (wt.%) |
|---|---|
| Polymer paste | 11~26 |
| Retarder | 11~22 |
| Plastic material | 15~26 |
| $BaTio_3$ powder | 26~63 |

[Fig. 6]

| Sample | Mixing Ratio (wt.%) |
|---|---|
| Black pigment | 1~5 |
| Polyurethane | 5~30 |
| Ethyllene glycon monoethyl ether acetate | 15~23 |
| Xylene | 50~71 |

[Fig. 7]

| Sample | Mixing Ratio (wt.%) |
|---|---|
| Polyurethane | 6~35 |
| Ethyllene glycon monoethyl ether acetate | 15~23 |
| Xylene | 50~71 |

CONTACT LIGHT EMITTING DEVICE

BACKGROUND OF THE INVENTION

This invention relates generally to a contact light emitting device, a method of manufacturing thereof and a contact input apparatus using thereof and more particularly, to a contact light emitting device, the method of manufacturing thereof and the contact input apparatus using thereof, capable of emitting a photo image of surface pattern of a contacted object upon contacting the object which acts as a ground and converting and outputting the emitted photo image to image signal such as an electrical image.

As a prior art, there is "an input apparatus using a fluorescent material" filed by the present application on May 19, 1997 as the Korea Patent Application No. 19282.

The input apparatus disclosed in the above application includes a metal electrode, a PN junction diode, a transparent conductive layer, an adhesive layer and a fluorescent film on a substrate formed with glass materials. The fluorescent film is formed with luminance material and is inputted with a various image pattern such as letters, figures, straight line, curve, etc., on the fluorescent film by way of pen or the like.

The fluorescent film is emitted to an image pattern inputted by way of a pen and the emitted light is converted from photo signal to the electrical signal through the PN junction diode. That is, the input signal is converted and outputted with the electrical signal after converting the input image pattern to photo signal.

However, it is possible to input surface pattern by way of the input apparatus. In other words, the input apparatus disclosed in the above application can input information by way of pushing and moving the pen to the flashing body film but cannot input information just by pushing the film. The input apparatus disclosed by the application thus cannot be used for recognition of fingerprints.

Accordingly, the present invention is disclosed to solve the aforementioned problem and it is an object of the present invention to provide a contact light emitting device by which an image of contacted area as well as an exact rough surface of contacted area can be lively expressed and generated in a light emitting image just by touch or contact to the light emitting apparatus.

SUMMARY OF THE INVENTION

It is an object of the present invention to provide a contact light emitting device capable of emitting photo image of surface pattern of a contacted object upon contacting the object which acts as a ground and a manufacturing method thereof.

It is other object of the present invention to provide a contact input apparatus capable of converting and outputting the photo images to the image signals such as electrical images.

Additional objects and advantages of the invention will set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, the contact light emitting device of this invention comprises a transparent electrode layer connected to one of alternating current power source terminals, luminescence layer for generating photo image such as surface pattern of contact surface by the electric field and formed between the transparent electrode layer and a contacted object which acts as a ground, a transparent insulating layer for penetrating the photo image and formed under the transparent electrode.

According to the present invention, a manufacturing method of a contact light emitting device of this invention comprising the steps of: forming a transparent insulating layer by using transparent insulating materials, forming a transparent electrode layer by using a transparent conductive material above the transparent insulating layer, and mixing 25–35 wt. % dielectric polymer paste, 25–29 wt. % retarder and 30–50 wt. % luminance powder doped by dopant above the transparent electrode layer and forming a luminescence layer by using the mixed compound.

A contact input apparatus of this invention comprises a transparent electrode layer connected to one of alternating current power source terminals, luminescence layer for generating photo image such as surface pattern of contact surface by the electric field and formed between the transparent electrode layer and a contacted object which acts as a ground, a transparent insulating layer for penetrating the photo image and formed under the transparent electrode, and a light receiving means for inverting an photo image occurred from the luminescence layer to an electrical signal received through the transparent electrode layer and the transparent insulating layer by attaching the transparent insulating adhesive material on a lower surface of the transparent insulating layer.

BRIEF DESCRIPTION OF THE DRAWINGS

These and other object, features, and advantages of the present invention will become more apparent from the following description of the preferred embodiments taken in conjunction with the accompanying drawings, in which.

DETAILED DESCRIPTION OF THE PREFERRED EMBODIMENT

The embodiments of a contact light emitting device according to present invention will now be described in detail based on the drawings.

Figure 1:
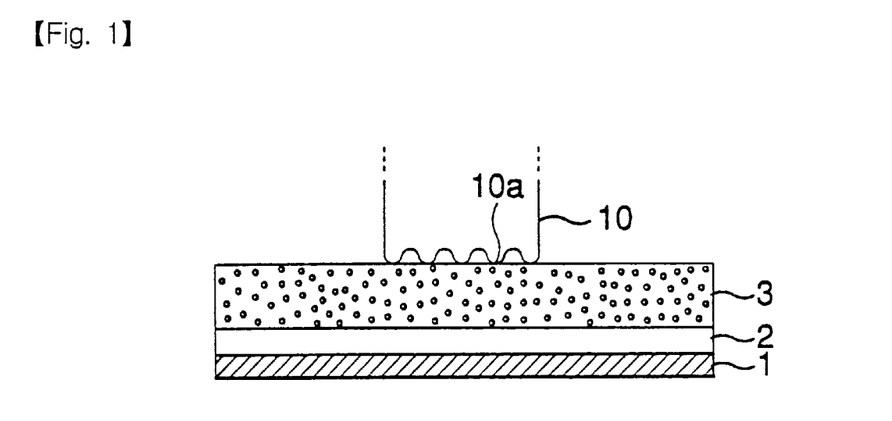
FIG. 1 is a sectional view showing a structure of a contact light emitting device in accordance with the present invention.

FIG. 1 is a sectional view showing a structure of a contact light emitting device in accordance with the present invention. The contact light emitting device of this invention comprises a transparent electrode layer 2 connected to one of alternating current power source terminals, a luminescence layer 3 for generating photo-image such as surface pattern of contact surface 10a by the electric field and formed between the transparent electrode layer 2 and a contacted object 10 upon contacting the object 10 which acts as a ground, and a transparent insulating layer 1 for penetrating the photo-image and formed under the transparent electrode 2.

In the FIG. 1, the transparent electrode layer 2 is formed on the transparent insulating layer 1 consisting of a transparent polymer. The transparent electrode layer 2 is formed with ITO (Indium Tin Oxide) and is connected to one of alternating current power source terminals. Also, a luminescence layer 3 is formed on the transparent electrode layer 2 to be connected to one of the alternating current power source terminals. The luminescence layer 3 is formed with luminance powder doped with dopant and dielectric polymer.

The luminance powder is formed with at least one among two elementary compound groups consisting of ZnS, SrS and ZnO. The dopant doped at the luminance powder is selected and mixed with at least one among dopant groups consisting of Mn, Cu, Cl, Al, I, Tb, and F.

The luminescence layer 3 is formed by adding a black pigment as an inorganic material for increasing contrast of photo image and is also formed by adding $BaTiO_3$ or other dielectric powders for increasing brightness thereof.

The black pigment contained within the luminescence layer 3 is generally existed at non-luminescence portion formed between a luminance powders. In case of emitting the luminance powder, the non-luminescence portion is changed to the darker state than before and maintained with said state to predetermined minutes by adding the black pigment. Therefore, the luminescence layer 3 can be made with high visual contrast of the photo image by providing a clear boundary between the luminance portion and the non-luminance portion.

An alternating current power source having 50–300V voltage and 1 K-3 MHz frequency is provided for the transparent electrode layer 2 for the purpose of activating the luminescence layer 3 with color and brightness which is determined by the dopant, the black pigment or $BaTiO_3$. The transparent electrode layer 2 is connected one of the alternating current power source terminals.

When the luminescence layer 3 is contacted by the object which acts as a ground, an electric field is formed between the object 10 and the transparent electrode layer 2 and a close circuit is formed through the object 10 to thereby emit the light.

That is, transparent electrode layer 2, luminescence layer 3 and the object 10 are formed with a close circuit upon contacting the object 10 which acts as a ground, and thus the electric field is formed at both ends of the luminescence layer 3.

When the luminescence layer 3 is activated by the electric field, a surface pattern of a contact surface 10a of the object 10 is generated with the photo image. Also, the photo image is generated with wavelength corresponding to visual light region. The photo image is entered into a downwardly direction through the transparent electrode layer 2 and the transparent insulating layer 1, and a transmitted photo image is used with various usage after processing with an image signal.

Also, the luminescence layer 3 for generating the photo image is formed by adding a dielectric layer (not shown) at one of an upper or a lower surfaces thereof. The dielectric layer is able to increase a capacitance of the contact light emitting device and thus the brightness is increased in proportion to an increment of the capacitance. The dielectric layer for increasing the luminance brightness is formed with one or multiple layer and the transparent insulating layer 1 is made of an insulating material in order to insulate and shield alternating current power source.

Figure 2:
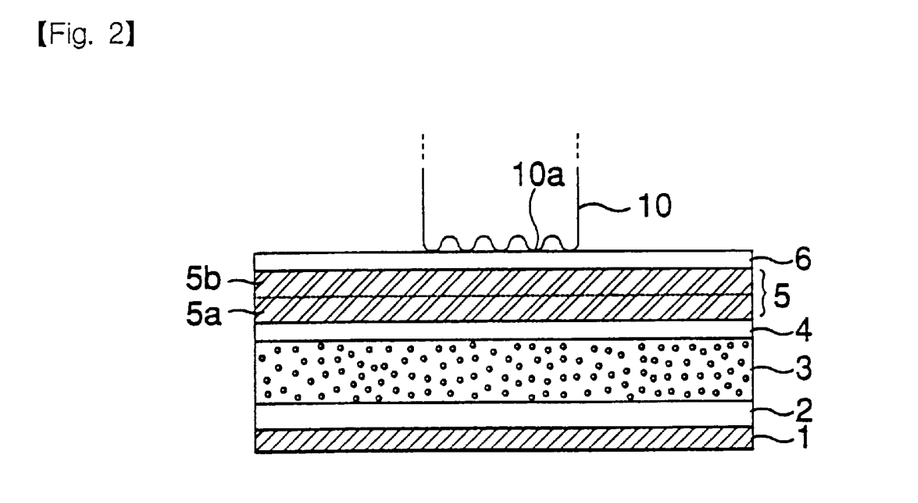
FIG. 2 is a sectional view showing a preferred embodiment of the contact light emitting device of FIG. 1.

FIG. 2 is a sectional view showing an embodiment of the contact light emitting device illustrated at FIG. 1. As shown in FIG. 2, a penetrating control layer 4, a shield layer 5 and water repellent layer 6 are gradually laminated on the luminescence layer 3.

The penetrating control layer 4 is formed between the luminance layer 3 and the shield layer 5 for controlling exactly an amount of a penetrated black pigment to the luminance layer 3. The penetrating control layer 4 is made of a dielectric polymer and $BaTiO_3$ so as to obtain a high dielectric ratio.

The penetrating control layer 4 is formed with a predetermined thickness in order to control the amount of the black pigment included at the shield layer 5. Also, the penetrating control layer 4 is acted as a dielectric layer by a dielectric polymer and $BaTiO_3$ powder. A shield layer 5 is formed between the penetrating control layer 4 and the water repellent layer 6.

The shield layer 5 is divided into a first shield layer 5a and second shield layer 5b for penetrating and forming a predetermined amount of black pigment to the luminescence layer 3 through the penetrating control layer 4 from the shield layer 5.

The second layer 5b is prevented from emitting the light existed at an outside of the contact emitting layer.

A water repellent layer 6 which includes an abrasive and a hydrophobic characteristics having a repulsive force to the water, is formed on the shield layer 5.

When the object 10 is contacted with the water repellent layer 6, the electric field is formed between the contacted object 10 and the transparent electrode layer 2 and thus generating the photo image by the electric field. The photo image is entered with downward direct ion through the transparent electrode layer 2 and the transparent insulating layer 1 and the entered photo image is used as various ways according to the contacted object 10.

Next, a manufacturing method of the contact light emitting device is described in more detail with reference to the accompanying drawing. The manufacturing method of the contact light emitting device is manufactured by using a thick or a thin film processes, respectively.

First, the manufacturing method of the contact light emitting device manufactured by using the thick film is described as follows.

The manufacturing of the contact light emitting device of the present invention comprising the steps of forming the transparent insulating layer 1 by using transparent insulating materials, forming the transparent electrode layer 2 by using a transparent conductive material above the transparent insulating layer 1, and mixing 25–35 wt. % dielectric polymer paste, 25–29 wt. % retarder and 30–50 wt. % luminance powder doped by dopant above the transparent electrode layer 2 and forming a luminescence layer by using the mixed compound.

The transparent insulating layer 1 is formed with a transparent insulating material containing a glass or a transparent polymer. The transparent insulating layer 1 is used as a substrate upon manufacturing the contact light emitting device and is gradually laminated and formed with the transparent electrode layer 2 and the luminescence layer 3 on the transparent insulating layer 1.

The transparent electrode layer 2 formed on the transparent insulating layer 1, is formed with a predetermined thickness by using a transparent conductive material as a paste type. The transparent conductive material for forming the transparent electrode layer 2, is formed by mixing an ITO (indium tin oxide) powder and a polymer.

Figure 3:
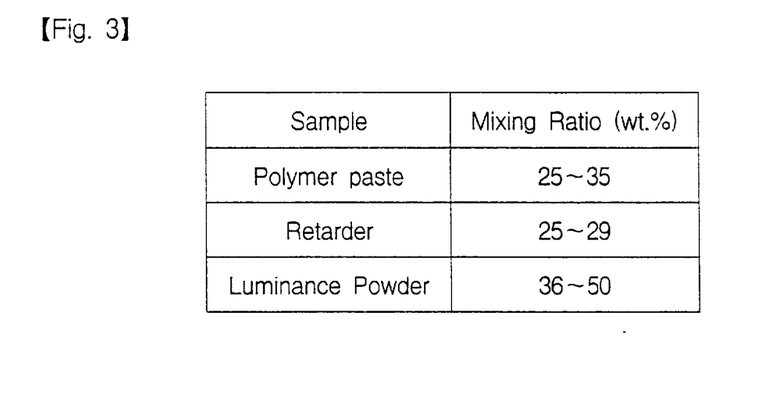
FIG. 3 is a table showing sample mixed ratios of a luminescence layer illustrating at FIGS. 1 and 2.

After forming the transparent electrode layer 2, the luminescence layer 3 is formed on the transparent electrode layer 2. As illustrated in FIG. 3, the luminescence layer 3 is formed with 25–35 wt. % dielectric polymer paste, 25–29 wt. % retarder, 30–50 wt. % luminance powder doped by dopant on a transparent electrode layer 2 and forming a luminescence layer 3 by using the mixed compound.

The luminance powder containing at the luminescence layer 3, is formed with at least one of two elementary compound groups consisting of ZnS, SrS and ZnO (for example, one of II–IV family compound groups). Also, the dopant doped at the luminance powder is formed with at least one of dopant groups consisting of Mn, Cu, Cl, Al, I, Tb, and F in order to control brightness and color thereof.

The dopant can be able to determine a luminance color of the luminescence layer 3. The luminescence color of the luminescence layer 3 is differently generated according to the dopant. Combinations of two elementary compound groups and the dopants include ZnS+Cu, Mn, Cl; ZnS+Cu; ZnS+Cu, I; ZnS+Cu, Cl; ZnS+Cu, Al.

Figure 4:
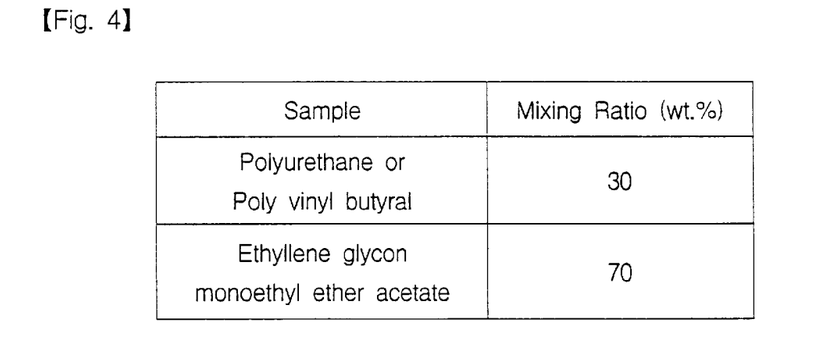
FIG. 4 is a table showing mixed ratios of polymer paste illustrated at FIG. 3.

A binder to be used as luminance powder doped by the dopant,is dielectric polymer paste. As illustrated in FIG. 4, the dielectric polymer paste is mixed and formed with 30 wt. % Poly (vinylbutyral-co-vinyl alcohol-co-vinyl acetate) and 70 wt. % ethyllene glycol mono-ethyl ether acetate. Also, it is formed by adding a retarder at the luminance powder. The retarder is formed with 20–60 $\mu$m thickness on the transparent electrode layer 2 for preventing, solidification of the luminescence layer 3 during screen printing process.

A dielectric layer (not shown)is added and formed on upper or lower surfaces of the luminescence layer 3 after forming the luminescence layer 3 above the transparent electrode layer 2. The dielectric layer is added and formed on one of the upper surface, the lower surface and both surfaces of the luminescence layer 3 after manufacturing the dielectric material as a paste type. The dielectric layer is formed as one or multiple layers.

As illustrated in FIG. 2, penetrating control layer 4, shield layer 5 and water repellent layer 6 are formed on the luminescence layer 3 for obtaining high brightness and having an abrasive or durability characteristics.

The dielectric polymer paste having a predetermined thickness is formed on the luminescence layer 3 before forming the penetrating control layer 4 on the luminescence layer 3. The polymer paste penetrates the luminescence layer 3 and coats the surface of the luminance powder to be formed the luminescence layer 3. The surface of the luminance powder is coated by the polymer so that the bulk of light occurred from the luminescence layer 3 cannot be dispersed to a distance. The light is remained by the polymer film coated at the surface of the luminance powder so that a good photo image can be obtained upon generating photo image.

Small quantities of black pigment and $BaTiO_3$ powder having molecular size not exceeding 1 $\mu$m, are added at the luminescence layer 3. The $BaTiO_3$ powder increases a dielectric ratio and the black pigment is to increase a non-luminance portion between the luminance portions and thus increasing the contrast of the photo image.

After finishing the coating process for covering the surface of the luminance power, it is dried at a dry oven (not shown) in order to volatilize and solidify the retarder. When the dry process is finished, the luminescence layer 3 is heated and pressurized under 100–200° C. and thus increasing a fineness of a membrane. After finishing the coating and drying processes, a penetrating control layer 4 is added and formed.

The penetrating control layer 4 is formed for controlling an amount of the black pigment at the process which penetrates the black pigment contained at a shield layer 5 to the luminescence layer 3.

Figure 5:
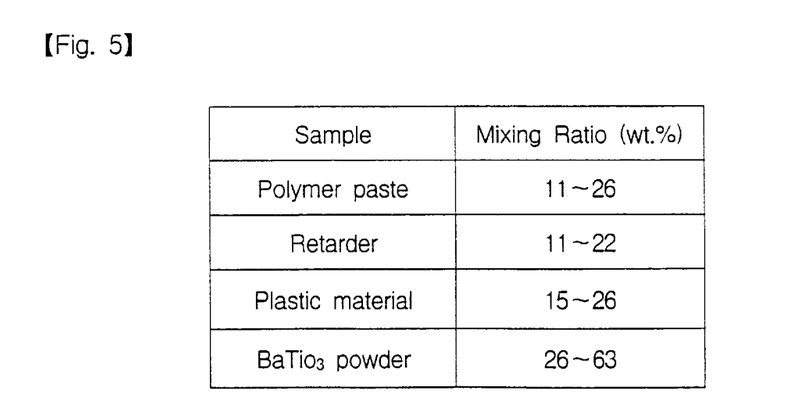
FIG. 5 is a table showing sample mixed ratios of a penetrating control layer illustrated at FIG. 2.

As illustrated in FIG. 5, the mixing ratio of penetrating control layer 4 is formed with 11–26 wt. % of polymer paste, 11–22 wt. % of retarder, 15–26 wt. % of plastic material and 26–63 wt. % of $BaTiO_3$ powder whose molecular size dose not exceed 1 $\mu$m. One of N-ethyl-P-toluenesulfonamide, dimethylformamide, dimethylphthalate for forming the luminescence layer 3 and the penetrating control layer 4 is selected and added to as the plastic material.

The penetrating control layer 4 having a thickness of approximately 5 $\mu$m is easily penetrated by the pigment contained at the shield layer 5 to the luminescence layer 3. In case of using the N-ethyl-P-toluenesulfonamide, the penetrating control layer 4 having high dielectric ratio is formed and is increased to the fineness of the membrane after heating and pressurizing under 100–200° C.

After forming the penetrating control layer 4, the shield layer 5 is formed above the penetrating control layer 4. If the penetrating, control layer 4 is not formed, the shield layer 5 is directly formed on the luminescence layer 3.

Figure 6:
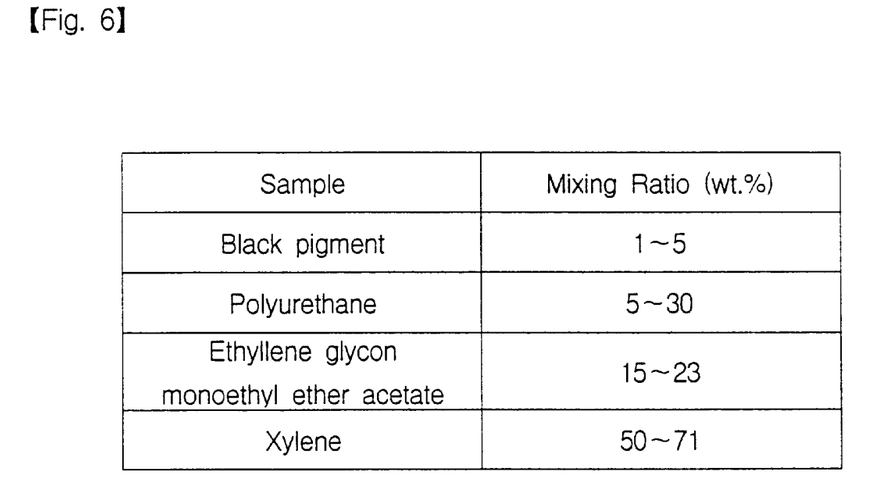
FIG. 6 is a table showing sample mixed ratios for manufacturing a shield layer illustrated at FIG. 2.

As illustrated in FIG. 6, the shield layer 5 is mixed and formed with 1–5 wt. % black pigment, 5–30 wt. % polyurethane, 15–23 wt. % ethyllene glycol monoethyl ether acetate, 50–71 wt. % xylene and $BaTiO_3$ powder whose molecular size does not exceeding 1 $\mu$m. The $BaTiO_3$ powder has more high dielectric ratio than the shield layer 5.

The shield layer 5 whose thickness does not exceeding 10 $\mu$m is formed. The shield layer 5 includes a first shield layer 5a penetrating and forming a predetermined amount of black pigment to the luminescence layer 3 wherein the first shield layer 5a has a lower viscosity than a second shield layer 5b, and a second shield layer 5b for shielding an outer light and formed above the first shield layer 5a. In the first shield layer 5a, the black pigment is penetrated and moved to the luminescence layer 3 through the penetrating control layer 4.

After forming the first shield layer 5a, the second shield layer 5b is formed. The black pigment contained at the second shield layer 5b is not to penetrate a light existed at an outer of the contact light emitting device into the luminescence layer 3. After forming the first shield layer 5a and the second shield layer 5b in regular sequence, the first and second shield layers 5a, 5b are increased to the fineness of the membrane by heating and pressurizing under 100–200° C. after polymerizing the first and second shield layers 5a, 5b at a dry oven.

A water repellent layer 6 whose thickness does not exceeding 5 $\mu$m is formed above the shield layer 5 constructed as the first shield layer 5a and the second shield layer 5b. The water repellent layer 6 is formed with a strong water repellent upon contacting one of a water, a moisture and an object and is also formed with a good internal abrasion for preventing an abrasion upon contacting the object.

Figure 7:
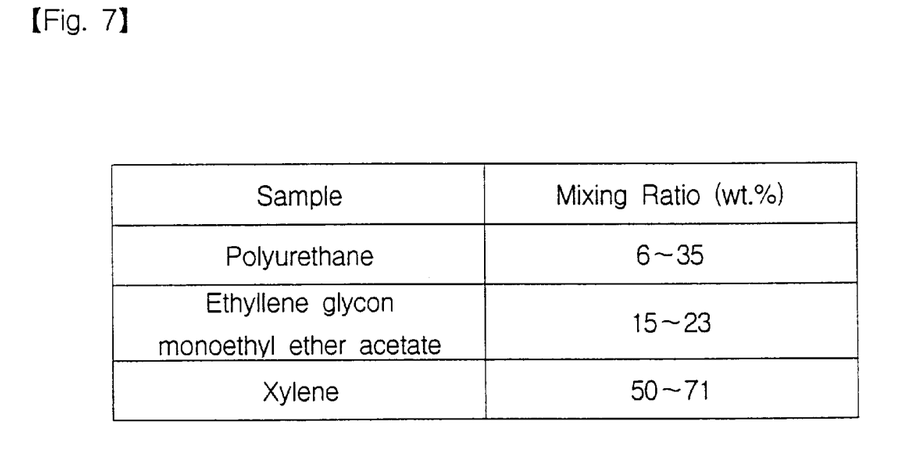
FIG. 7 is a table showing sample mixed ratios for manufacturing a water repellent layer illustrated at FIG. 2.

As illustrated in FIG. 7, the water repellent layer 6 is mixed and formed with 6–35 wt. % polyurethane, 15–23 wt. % ethylene glycol mono ethyl ether acetate, 50–71 wt. % xylene and $BaTiO_3$ on the shield layer and forming a water repellent layer.

Upon forming the penetrating control layer 4, the polyurethane can be replaced with a poly(vinyl butyral-co-vinyl alcohol-co-vinyl acetate).

The above mentioned method is a manufacturing method of the contact light emitting device using a thick film to be formed by using a screen printing method or a spin coating method.

A plain degree of the membrane of the spin coating method is improved rather than that of the screen printing method. The contact light emitting device of the present invention is also manufactured by using thin film.

Each of materials of the layers for forming the contact light emitting device is formed with solidification. That is, each of the layers is formed with sputtering target or solidification in order to manufacture the contact light emitting device with thin film.

As illustrated in FIG. 1, the transparent electrode layer 2 having 0.05–0.1 μm thickness is formed after sputtering the ITO manufactured by the sputtering target on the transparent insulating layer 1. After forming the transparent electrode layer 2, the luminescence layer 3 having 0.5–1.0 μm thickness is formed by sputtering the sputtering target for forming the luminescence layer 3 on the transparent electrode layer 2.

The mixing example of the target for forming the luminescence layer 3 is formed with ZnS+Mn, Cl; ZnS+Tb, F; SrS+Ce, etc. A concentration of the dopant to be doped at the luminance powder manufactured by the sputtering method is 0.1–2.5 atomic %.

A dielectric layer (not shown) formed at least one surface of the luminescence layer 3 is used as a target with a high dielectric material. The dielectric layer having 0.3–0.5 μm thickness is formed by sputtering as a target with the high dielectric material on the transparent electrode layer 2 or the luminescence layer 3. After forming the shield layer 5 and the water repellent layer 6 by using the sputtering target, the shield layer 5 and the water repellent layer 5 are formed with sputtering order, respectively. Also, the contact light emitting device is also manufactured by an evaporation method after forming material of each layer with solidification in replace of the sputtering method.

Now, a contact input apparatus for converting and outputting the photo image occurred at the contact light emitting device manufactured by using thick film or thin film methods to the image signal such as an electrical signal will be described in more detail with reference to accompanying drawings.

Figure 8:
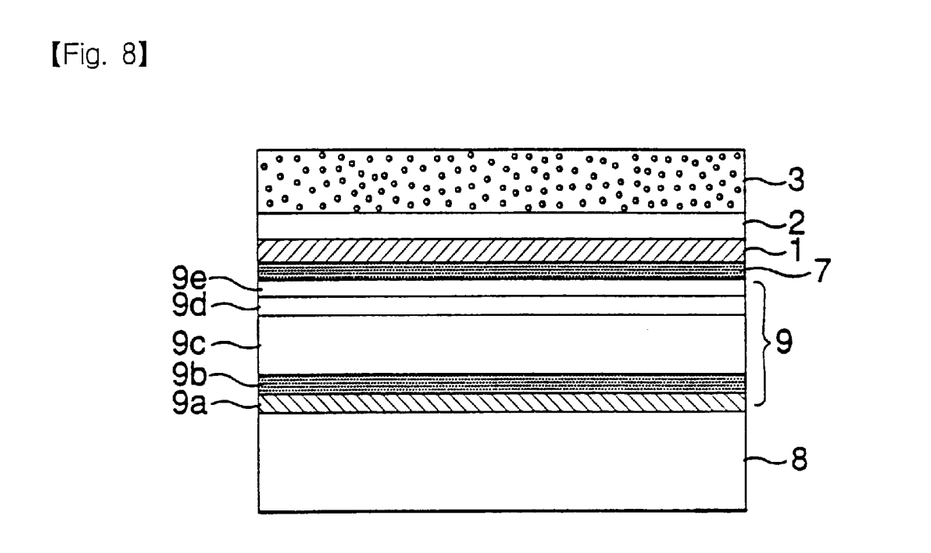
FIG. 8 is a sectional view of a structure of contact input apparatus using contact light emitting device in accordance with the present invention.
Figure 9:
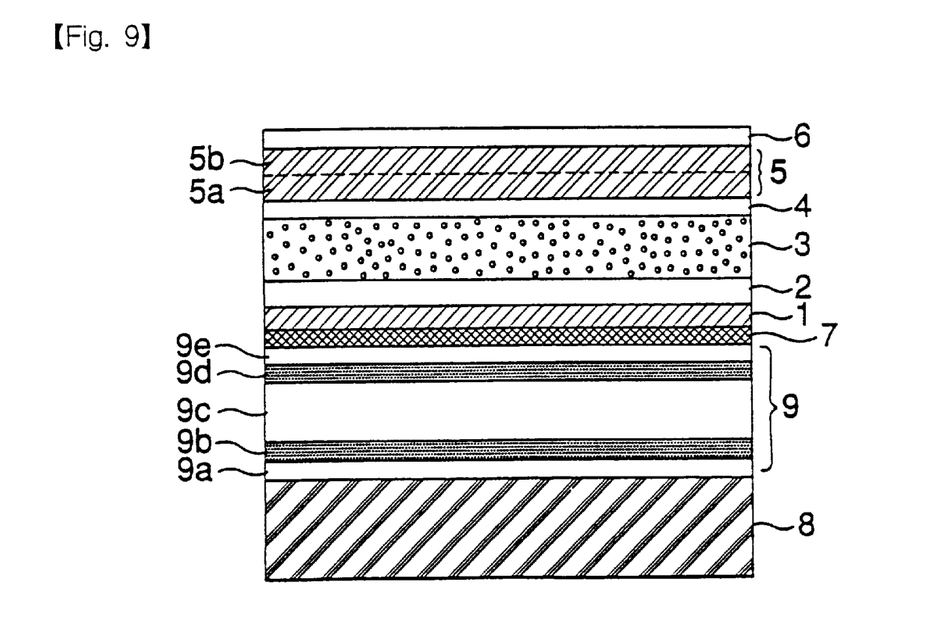
FIG. 9 is a sectional view showing a preferred embodiment of the contact input apparatus using contact light emitting device in accordance with the present invention.

FIG. 8 is a sectional view for illustrating the structure of the contact input apparatus using the contact light emitting device of the present invention and FIG. 9 is a sectional view shown an embodiment of the contact input apparatus using the contact light emitting device of the present invention. As shown in FIGS. 8 and 9, when the object 10 is contacted with the transparent electrode layer 2 connected to one of alternating current power source terminals, the electric field is formed between the transparent electrode layer 2 connected to one of alternating current power terminals and the contacted object 10.

The contact input apparatus including the transparent electrode layer 2 connected to one of alternating current power source terminals, luminescence layer 3 for generating photo-image such as surface pattern of contact surface by electric field and formed between the transparent electrode layer 2 and a contacted object 10 which acts as a ground, a transparent insulating layer 1 for penetrating the photo-image and formed under the transparent electrode layer 2, and a light receiving element 9 for inverting an photo-image occurred from the luminescence layer 3 to an electrical signal received through the transparent electrode layer 2 and the transparent insulating layer 1 by attaching the transparent insulating adhesive material 7 on a lower surface of the transparent insulating layer 1.

Referring to FIG. 1, the contact input apparatus is constructed with the transparent insulating layer 1, the transparent electrode layer 2 and luminescence layer 3. Also, the penetrating control layer 4, the shield layer 5 and the water repel lent layer 6 are formed on the luminescence layer 4 as shown in FIG. 2. A contact input apparatus can be constructed with a constructing element of the contact light emitting device shown in FIGS. 1 and 2 and the light receiving element 9 as the transparent insulating adhesive material 7.

The contact input apparatus is formed by attaching the transparent insulating of the contact light emitting device and by using transparent insulating adhesive material 7 to the light receiving element 9 formed on a substrate 8. The light receiving element 9 formed on the substrate 8 is a PN junction diode.

For converting the received photo-image to the electrical signal, the PN junction diode is formed with a solar cell structure and regularly laminated to a lower electrode layer 9a formed with a conductive metal on the substrate 8, N-type amorphous silicon layer 9b, an intrinsic amorphous silicon layer 9c, P-type amorphous silicon layer 9d and an upper transparent electrode layer 9e, respectively.

The electric field is formed by applying a predetermined reversed direct ion voltage to the PN junction diode. A pair of electron holes which generates in the PN junction diode, is separated by the received photo-image and the electric signal according to the separated photo-image is occurred. The photo-image is received at P-type amorphous silicon layer 9d so that intrinsic amorphous silicon layer 9c such as depletion layer is also occurred. Since the pair of electron holes is separated by the electric field, the holes are moved to the upper transparent electrode layer 9e through the P-type amorphous silicon layer 9d and electron is moved to the lower electrode layer 9a through the N-type amorphous silicon layer 9b and an electric signal according to the photo-image is occurred.

The light receiving element is formed with two dimensional array for receiving the photo-image occurred at the contact light emitting device. In the light receiving element having the two dimensional array, an array number of the light receiving element is determined by an analysis performance of the contacted object 10 and a resolution of the contacted surface 10a of the object 10 is differently formed to the array number of the light receiving element. The light receiving element such as PN junction diode can be replaced with CCD(Charge Coupled Device) sensor or CMOS (Complementary Metal Oxide Semiconductor) image sensor.

A photo-image generated at the contact light emit ting device formed by using the luminance powder consisted with two elementary compound groups is converted to the electric signal by the light receiving element. Thus, a pattern of a contact surface of the object is converted to an image signal.

When an object (for example, a fingerprint formed at a finger of the human) is loaded on the contact surface of the contact light emitting device, a concave and convex pattern formed at the contacted object is automatically extracted from photo-image and converted into an image signal. According to the present invention, the clear surface pattern of a contacted object can be obtained by generating the photo-image such as a surface pattern of the object which acts as a ground and converting the photo-image to an image signal such as an electric signal. Thus, the present invention can be applied to a fingerprint identification system, which compares the difference between a stored fingerprint data and a detected fingerprint. Also, the present invention enables a reduced manufacturing cost by using a screen printing method.

The invention is no way limited to the embodiment described hereinabove. Various modifications of the disclosed embodiment as well as other embodiments of the invention will become apparent to persons skilled in the art upon reference to the description of the invention. It is therefore contemplated that the appended claims will cover any such modifications or embodiments as fall within the true scope of the invention.

What is claimed is:

1. A contact light emitting device comprising:
   a transparent insulating layer;
   a transparent electrode layer overlaying said transparent insulating layer;
   a luminescence layer overlaying said transparent electrode layer; and
   a stray light shield layer overlaying said luminescence layer, wherein the luminescence layer and the electrode layer are configured such that an electric field can be generated between an object to be imaged and said transparent electrode layer.

2. The contact light emitting device according to claim 1, wherein said transparent electrode layer comprises Indium Tin Oxide.

3. The contact light emitting device according to claim 1, wherein said luminescence layer comprises a luminance compound, a dopant, and at least one dielectric material.

4. The contact light emitting device according to claim 3, wherein said luminance compound comprises at least one compound selected from the group consisting of ZnS, SrS, and ZnO.

5. The contact light emitting device according to claim 3, wherein said dopant comprises at least one material selected from the group consisting of manganese, copper, chlorine, aluminum, iodine, terbium, and fluorine.

6. The contact light emitting device according to claim 3, wherein said dielectric material comprises a polymer.

7. The contact light emitting device according to claim 1, wherein the luminescence layer includes $BaTiO_3$.

8. The contact light emitting device according to claim 1, wherein said luminescence layer includes a dark pigment that acts to enhance contrast.

9. The contact light emitting device according to claim 1, further comprising at least one dielectric layer formed on at least one of an upper and lower surface of said luminescence layer.

10. The contact light emitting device according to claim 1, further comprising a penetrating control layer formed between said luminescence layer and said stray light shield layer, wherein said stray light shield layer includes a dark pigment material, and wherein said penetrating control layer is configured to limit an amount of said dark pigment that passes from said stray light shield layer to said luminescence layer.

11. The contact light emitting device according to claim 10, wherein said penetrating control layer comprises a dielectric polymer material and $BaTiO_3$.

12. The contact light emitting device of claim 10, wherein said stray light shield layer comprises:
    a first layer adjacent the penetrating control layer that includes said dark pigment material; and
    a second layer overlying said first layer, wherein said second layer is configured to block exterior light.

13. A contact light emitting device comprising:
    a transparent insulating layer;
    a transparent electrode layer overlaying said transparent insulating layer;
    a luminescence layer overlaying said transparent electrode layer; and
    a protective layer overlaying said luminescence layer, wherein said luminescence layer and said electrode layer are configured such that an electric field can be generated between an object to be imaged and said transparent electrode layer.

14. The contact light emitting device according to claim 13, wherein said transparent electrode layer comprises Indium Tin Oxide.

15. The contact light emitting device according to claim 13, wherein said luminescence layer comprises a luminance compound, a dopant, and at least one dielectric material.

16. The contact light emitting device according to claim 10, wherein said luminance compound comprises at least one compound selected from the group consisting of ZnS, SrS, and ZnO.

17. The contact light emitting device according to claim 10, wherein said dopant comprises at least one material selected from the group consisting of manganese, copper, chlorine, aluminum, iodine, terbium, and fluorine.

18. The contact light emitting device according to claim 15, wherein said dielectric material comprises a polymer.

19. The contact light emitting device according to claim 13, wherein the luminescence layer comprises $BaTiO_3$.

20. The contact light emitting device according to claim 13, wherein said luminescence layer includes a dark pigment that acts to enhance contrast.

21. The contact light emitting device according to claim 13, further comprising at least one dielectric layer formed on at least one of an upper surface and a lower surface of said luminescence layer.

22. The contact light emitting device according to claim 13, wherein said protective layer is hydrophobic.

23. The contact light emitting device according to claim 13, wherein said protective layer is abrasion resistant.

24. The contact light emitting device according to claim 13, further comprising a shield layer disposed between said protective layer and said luminescence layer, wherein said shield layer is configured to block exterior light.

25. The contact light emitting device according to claim 24, further comprising a penetrating control layer formed between said shield layer and said luminescence layer.

26. The contact light emitting device according to claim 25, wherein said shield layer comprises:
    a first layer adjacent the penetrating control layer that includes a dark pigment; and
    a second overlaying said first layer and configured to block exterior light.

27. A contact light emitting device comprising:
    a transparent insulating layer;
    a transparent electrode layer overlaying said transparent insulating layer; and a luminescence layer overlaying said transparent electrode layer, wherein the electrode layer is configured such that an electric field can be generated between an object to be imaged and said transparent electrode layer, and wherein said electric field causes said luminescence layer to luminesce when the object to be imaged is brought adjacent to said luminescence layer.

28. The contact light emitting device according to claim 27, wherein the luminescence layer includes $BaTiO_3$, which acts to enhance contrast.

29. The contact light emitting device according to claim 27, wherein said luminescence layer further comprises a dark pigment that acts to increase contrast.

30. The contact light emitting device according to claim 27, further comprising at least one dielectric layer formed on at least one of an upper and a lower surface of said luminescence layer.

31. The contact light emitting device according to claim 27, further comprising a shield layer overlaying said luminescence layer, wherein the shield layer is configured to block exterior light.

32. The contact light emitting device of claim 27, further comprising a protective layer overlaying said luminescence layer.

33. The contact light emitting device of claim 32, wherein said protective layer repels moisture.

34. The contact light emitting device of claim 32, wherein said protective layer is abrasion resistant.

35. The contact light emitting device of claim 27, further comprising:

a shield layer that includes a dark pigment; and a penetrating control layer 1 located between said shield layer and said luminescence layer, wherein said penetrating control layer is configured to limit an amount of the dark pigment in the shield layer that migrates to the luminescence layer.

36. The contact light emitting device of claim 35, wherein the shield layer is also configured to block external light.

37. The contact light emitting device of claim 35, further comprising a protective layer overlying the shield layer, wherein the protective layer is abrasion resistant and repels moisture.

* * * * *